US009835782B2

(12) United States Patent
Ito et al.

(10) Patent No.: US 9,835,782 B2
(45) Date of Patent: Dec. 5, 2017

(54) IRRADIATION MODULE HAVING LIGHT GUIDES

(71) Applicant: OLYMPUS CORPORATION, Tokyo (JP)

(72) Inventors: Takeshi Ito, Hino (JP); Eiji Yamamoto, Musashimurayama (JP); Masahiro Nishio, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 270 days.

(21) Appl. No.: 14/301,704

(22) Filed: Jun. 11, 2014

(65) Prior Publication Data

US 2014/0293641 A1 Oct. 2, 2014

Related U.S. Application Data

(63) Continuation of application No. PCT/JP2012/082073, filed on Dec. 11, 2012.

(30) Foreign Application Priority Data

Dec. 13, 2011 (JP) ................................ 2011-272562

(51) Int. Cl.
*F21V 8/00* (2006.01)
*A61B 1/00* (2006.01)
(Continued)

(52) U.S. Cl.
CPC ........ *G02B 6/0005* (2013.01); *A61B 1/00096* (2013.01); *A61B 1/00117* (2013.01);
(Continued)

(58) Field of Classification Search
CPC .. G02B 6/0005; G02B 6/0008; G02B 6/0006; G02B 6/42; G02B 6/4215;
(Continued)

(56) References Cited

U.S. PATENT DOCUMENTS 5,196,928 A * 3/1993 Karasawa ............ A61B 1/0005
348/239
7,179,222 B2 * 2/2007 Imaizumi ........... A61B 1/00009
600/109
(Continued)

FOREIGN PATENT DOCUMENTS

CN 201731334 U 2/2011
JP 10-225426 A 8/1998
(Continued)

OTHER PUBLICATIONS

Chinese Office Action dated Aug. 21, 2015 issued in CN 201280061826.8.
(Continued)

*Primary Examiner* — Anh Mai
*Assistant Examiner* — Arman B Fallahkhair
(74) *Attorney, Agent, or Firm* — Scully, Scott, Murphy & Presser, P.C.

(57) ABSTRACT

An irradiation module mechanically detachably attached to a light source module includes a first light source light entrance end which allows entry of first light source light from a first light source module, a first light guide member to guide the first light source light entered the first light source light entrance end, a second light source light entrance end which allows entry of second light source light from a second light source module, and a second light guide member to guide the second light source light entered the second light source light entrance end. The first light guide member and the second light guide member have optical specifications which correspond to optical characteristics of the light source light to be guided and in which the optical characteristics are different from each other.

33 Claims, 3 Drawing Sheets

(51) Int. Cl.
*A61B 1/07* (2006.01)
*A61B 1/06* (2006.01)

(52) U.S. Cl.
CPC .......... *A61B 1/0638* (2013.01); *A61B 1/0653* (2013.01); *A61B 1/07* (2013.01)

(58) Field of Classification Search
CPC ............ A61B 1/00096; A61B 1/00117; A61B 1/0638; A61B 1/0653; A61B 1/07
USPC ......... 362/553, 259, 84, 231, 551, 555, 574, 362/510, 554, 184
See application file for complete search history.

(56) References Cited

U.S. PATENT DOCUMENTS

| | | | | |
|---|---|---|---|---|
| 7,367,682 | B2 * | 5/2008 | Dvorkis | G03B 21/28 348/205 |
| 7,556,439 | B2 * | 7/2009 | Nakanishi | G02B 6/4246 385/24 |
| 7,672,041 | B2 * | 3/2010 | Ito | A61B 1/0638 359/326 |
| 8,506,478 | B2 * | 8/2013 | Mizuyoshi | A61B 1/0638 250/458.1 |
| 8,936,548 | B2 * | 1/2015 | Ozawa | A61B 1/0638 600/178 |
| 2008/0310181 | A1 | 12/2008 | Gurevich et al. | |
| 2009/0097806 | A1 | 4/2009 | Viellerobe et al. | |
| 2009/0306478 | A1 | 12/2009 | Mizuyoshi | |

FOREIGN PATENT DOCUMENTS

| | | |
|---|---|---|
| JP | 10-243915 A | 9/1998 |
| JP | 10-337271 A | 12/1998 |
| JP | 2004-097442 A | 4/2004 |
| JP | 2005-292670 A | 10/2005 |
| JP | 2006-047622 A | 2/2006 |
| JP | 2006-204341 A | 8/2006 |
| JP | 2006-288534 A | 10/2006 |
| JP | 2010-160948 A | 7/2010 |
| JP | 2011-505171 A | 2/2011 |
| JP | 2011-206227 A | 10/2011 |

OTHER PUBLICATIONS

Japanese Office Action dated Nov. 4, 2015 from related Japanese Patent Application No. 2011-272562, together with an English language translation.
Extended Supplementary European Search Report dated Dec. 15, 2015 from related European Application No. 12 85 8531.2.
Supplementary Partial European Search Report dated Jul. 27, 2015 from related European Application No. 12 85 8531.2.
English translation of International Preliminary Report on Patentability together with the Written Opinion dated Jun. 26, 2014 received in related International Application No. PCT/JP2012/082073.
International Search Report dated Feb. 5, 2013 issued in PCT/JP2012/082073.
Japanese Decision of Rejection dated Jun. 28, 2016 received in Japanese Patent Application No. 2011-272562, together with an English-language translation.
European Office Action dated Apr. 28, 2017 received in European Application No. 12 858 531.2.
Chinese Office Action dated Nov. 1, 2016 received in Chinese Patent Application No. 201280061826.8, together with an English-language translation.
Chinese Office Action dated Jun. 14, 2017 received from Chinese Application No. 201280061826.8, together with an English-language translation.

* cited by examiner

IRRADIATION MODULE HAVING LIGHT GUIDES

CROSS-REFERENCE TO RELATED APPLICATIONS

This application is a Continuation application of PCT Application No. PCT/JP2012/082073, filed Dec. 11, 2012 and based upon and claiming the benefit of priority from the prior Japanese Patent Application No. 2011-272562, filed Dec. 13, 2011, the entire contents of which are incorporated herein by reference.

BACKGROUND OF THE INVENTION

1. Field of the Invention

The present invention relates to an irradiation module having light guide members.

2. Description of the Related Art

As one example of a light source system on which two types of light sources and two types of light guide members corresponding to these light sources are mounted, there is disclosed in, for example, Jpn. Pat. Appln. KOKAI Publication No. H10-337271, a fluoroendoscope in which a laser light source and a usual illuminating light source are combined. This fluoroendoscope is constituted so that usual illuminating light and laser light can be applied onto a living tissue, and the image light obtained during the irradiation with the usual illumination and fluorescence obtained by a TV camera during the irradiation with the laser light can be observed via an image bundle. More specifically, the laser light is guided to a tip of an endoscope by use of an optical fiber for laser transmission, and the usual illuminating light is guided to the tip of the endoscope by use of an optical fiber bundle for usual illumination. In the above Jpn. Pat. Appln. KOKAI Publication No. H10-337271, there is described a structure where bare fibers of the optical fiber bundle for usual illumination are wound around the optical fiber for laser transmission.

As seen in the above-mentioned constitution example of a fluoroendoscope, a light source system on which two types of light sources and two types of light guide members corresponding to these light sources are mounted has the following problem. That is, exclusive and special light guide mechanisms corresponding to the respective light sources are required, and it is necessary to individually construct the exclusive light source system for each purpose (a usual illuminating light source system and a laser light source system for fluorescent observation in the case of the above Jpn. Pat. Appln. KOKAI Publication No. H10-337271). Therefore, the conventional light source system is expensive and has poor cost performance.

BRIEF SUMMARY OF THE INVENTION

The present invention has been developed in view of the above, and an object thereof is to provide an irradiation module capable of coping with various purposes without having to construct a separate dedicated system.

According to an aspect of the invention, there is provided an irradiation module mechanically detachably attached to a light source module, comprising:

a first light source light entrance end which allows entry of first light source light emitted from a first light source module;

a first light guide member to guide the first light source light which has entered the first light source light entrance end;

a second light source light entrance end which allows entry of second light source light emitted from a second light source module different from the first light source module; and a second light guide member to guide the second light source light which has entered the second light source light entrance end, wherein the first light guide member and the second light guide member have optical specifications which correspond to optical characteristics of the light source light to be guided and in which the optical characteristics are different from each other.

According to the present invention, an irradiation module has light guide routes to emit illuminating light for each purpose. In other words, the irradiation module has light guide members to appropriately guide light emitted from a light source in accordance with a type of light source, whereby it is possible to provide the irradiation module capable of coping with various purposes without having to construct a separate dedicated system.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

MODE FOR CARRYING OUT THE INVENTION

Detailed Description of the Invention

First Embodiment

Figure 1:
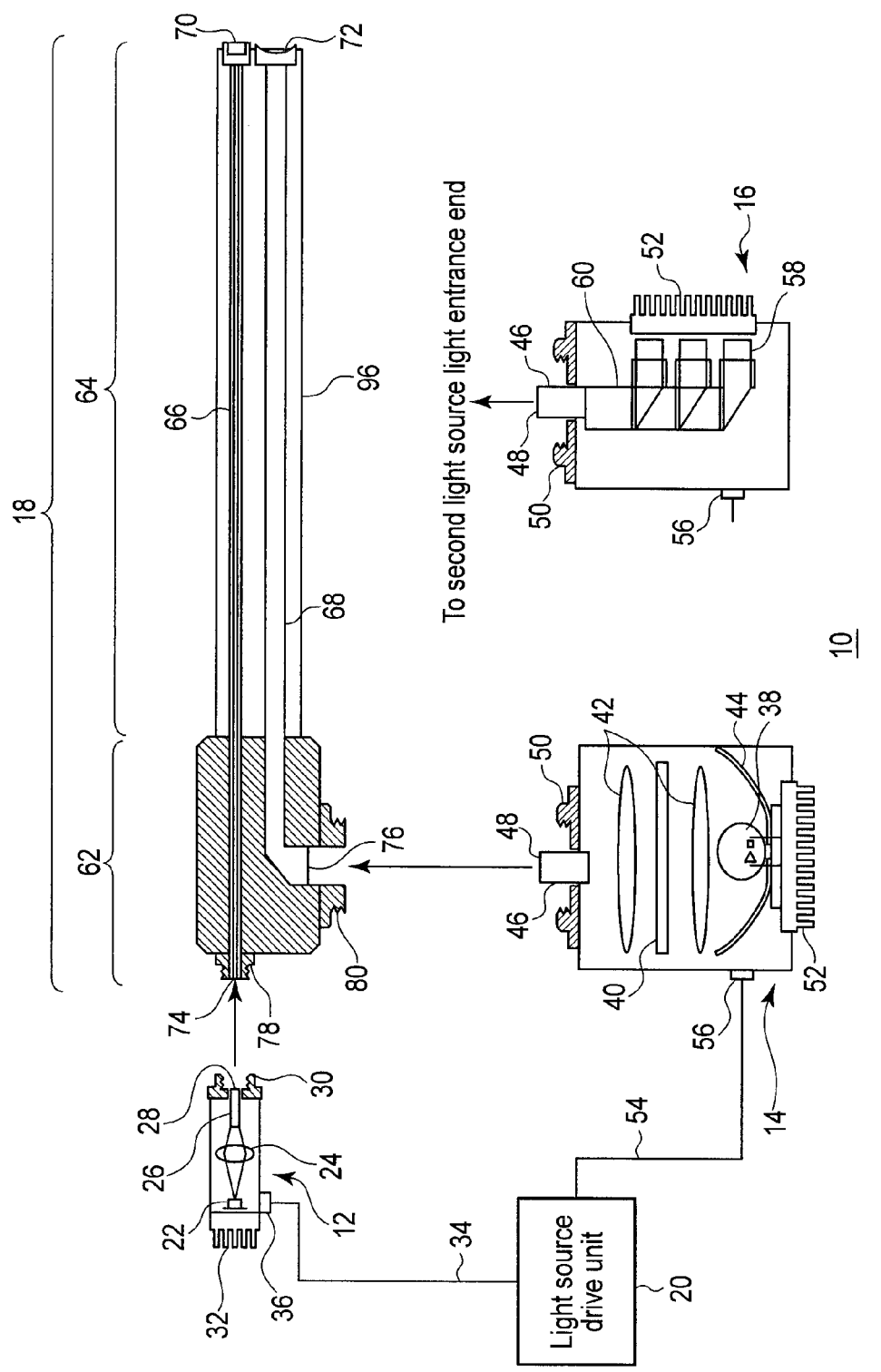
FIG. 1 is a view showing a constitution of a light source system to which an irradiation module having light guide members according to a first embodiment of the present invention is applied.

FIG. 1 is a view showing a constitution of a light source system to which an irradiation module having light guide members according to a first embodiment of the present invention is applied.

As shown in FIG. 1, this light source system 10 is constituted of three light source modules (a first light source module 12, a second light source module 14, and a third light source module 16), and one irradiation module 18 according to the present embodiment. That is, the irradiation module 18 is combined with an appropriate light source module selected from the three light source modules 12, 14, and 16, so that it is possible to construct a light source device capable of emitting illuminating light for each purpose.

Next, respective elements constituting the above light source system 10 will be described in order.

First, the light source modules 12, 14, and 16 are described.

Each of the first to third light source modules 12, 14, and 16 includes a light source which emits light source light, a light source light emitting end which emits the light source light emitted from the light source, toward an after-mentioned light source light entrance end of the irradiation module 18, and a fixing portion A 30 to attach the light source light emitting end to an after-mentioned connection unit of the irradiation module 18. Furthermore, the light source module has an electric terminal which is electrically connected to a light source drive unit 20 to drive each light source, and receives, from the light source drive unit 20, a power and a control signal to allow the light source to emit the light.

Hereinafter, the separate light source modules 12, 14, and 16 will be described.

First, the first light source module 12 is described.

On the first light source module 12, a blue semiconductor laser light source 22 of an InGaN series which emits blue laser light is mounted as a first light source. The blue laser light emitted from the blue semiconductor laser light source 22 is condensed via a lens 24, and a large part of the light enters a laser light guiding optical fiber 26. An emitting end of the laser light guiding optical fiber 26 is a first light source light emitting end 28. The first light source light emitting end 28 is constituted to be optically connectable to an after-mentioned first light source light entrance end of the connection unit (which will be described later) disposed in the irradiation module 18. The first light source module 12 and the connection unit have a mechanically holdable connection mechanism. That is, a first fixing portion A 30 disposed in the vicinity of the first light source light emitting end 28 of the first light source module 12 is constituted to engage with an after-mentioned first fixing portion B 78 disposed in the vicinity of the first light source light entrance end of the connection unit, and the first light source module 12 and the connection unit are mechanically held.

Furthermore, the first light source module 12 has a heat radiation mechanism 32 in which a Peltier element and a heat radiation fin are combined to radiate heat generated from the blue semiconductor laser light source 22 as the first light source. In the drawing, for simplicity, only the heat radiation fins are depicted, and the Peltier element and a control system of the element are omitted.

Furthermore, the first light source module has an electric terminal 36 to be electrically connected to the light source drive unit 20 via a connection cable 34.

Next, the second light source module 14 will be described.

On the second light source module 14, an Xe lamp 38, which is a type of electric discharge lamp, is mounted as a white light source which is a second light source. In the lamp light discharged from the Xe lamp 38, a forward discharged component is condensed via a filter 40 and lenses 42 and further, a rearward discharged component is condensed via a mirror 44, the filter 40 and the lenses 42, and part of these components enters a light guide rod 46. In the two lenses 42, the lens on the side of the Xe lamp 38 has a function of forming the lamp light into substantially parallel light, so that the lamp light formed into the substantially parallel light is applied onto the filter 40. The filter 40 is a band pass filter or a combination of a low pass filter and a high pass filter, which has a function of removing unnecessary ultraviolet and infrared rays from the lamp light discharged from the Xe lamp 38. In the two lenses 42, the lens disposed on the side of the light guide rod 46 has a function of condensing the lamp light from which unnecessary components are removed by the filter at an entrance end of the light guide rod 46. Furthermore, the mirror 44 is a concave surface mirror having a function of reflecting the rearward discharged lamp light toward the lenses 42 to condense the light on the lenses 42. An emitting end of the light guide rod 46 is a second light source light emitting end 52. The second light source light emitting end 52 is constituted to be optically connectable to a later-mentioned second light source light entrance end of the connection unit (described later) of the irradiation module 20 or 22. The second light source module 14 and the connection unit have a mechanically holdable connection mechanism. That is, a second fixing portion A 50 mounted on the second light source module 14 engages with a later-mentioned second fixing portion B 80 mounted on the connection unit, to constitute the connection mechanism mechanically holding both of the second light source module 14 and connection mechanism. Furthermore, on the second light source module 14, a heat radiation mechanism is mounted in which a cooling fan and heat radiation fins 52 are combined to radiate heat generated from the Xe lamp 38, and heat of a member irradiated with the lamp light to absorb a part of the lamp light and raise its temperature. It is to be noted that in the drawing, for simplicity, only the heat radiation fins 52 are depicted, and the cooling fan, a related control system and the like are omitted.

Furthermore, the second light source module has an electric terminal 56 to be electrically connected to the light source drive unit 20 via a connection cable 54.

Next, the third light source module 16 will be described.

Basically, on the third light source module 16, LEDs 58 are mounted to constitute a third light source, in place of the Xe lamp 38 which is the second light source mounted on the second light source module 14. The third light source module 16 is different from the second light source module 14 in that the Xe lamp 38 is replaced with the LEDs 58 and in a constitution of an optical system for allowing the light source light to enter a light guide rod 46. The third light source module 16 is constituted so that the LEDs 58 of three colors of RGB are mounted on the same substrate, and LED light generated from the respective LEDs 58 is condensed in one optical path by a multiplexing optical system 60, to enter the light guide rod 46. The multiplexing optical system 60 is constituted by using dichroic mirrors or the like. As the substrate on which the LEDs 58 are mounted, an aluminum substrate, an aluminum nitride substrate or the like having a high thermal conductivity is used, and heat radiation fins 52 are disposed on a back surface of the substrate. It is to be noted that even in the case of the LEDs 58, heat of the LEDs can be more efficiently radiated by using a cooling fan, and hence this cooling fan may be mounted. Furthermore, also in the case of the LEDs 58, a light condensing lens or a filter to cut unnecessary LED light may be used in accordance with a purpose.

Furthermore, in the same manner as in the above second light source module 14, the third light source module has an electric terminal 56 to be electrically connected to the light source drive unit 20 via the connection cable 54.

In the third light source module 16, a light intensity ratio of the R light, the G light and the B light is regulated, whereby illuminating light of various colors can be realized. White light can be realized by mixing an equal intensity of each light.

It is to be noted that the third light source module 16 has a basic functional constitution similar to the second light source module 14, and hence in the subsequent description, an example where the second light source module 14 is used will be described as a representative, and description of a constitution or an operation of the third light source module 16 is omitted.

Next, the light source drive unit 20 will be described.

The light source drive unit 20 is a unit which supplies power to the light source modules 12 and 14 (16) having such constitutions as described above, and controls emission states of the light sources to be mounted on the light source modules 12 and 14 (16). The light source system 10 in the present embodiment includes one light source drive unit 20 which is electrically connectable to both of the first light source module 12 and the second light source module 14 via the connection cables 34 and 54 and the electric terminals 36 and 56.

The light source drive unit 20 has a function of discriminating types of the connected light source modules 12 and 14 (16). That is, on the connection cables 34 and 54 of the light source drive unit 20 to the light source modules 12 and 14 (16), a discrimination signal wiring line to discriminate the types of the connected light source modules 12 and 14 (16) is mounted, in addition to a power wiring line to supply the power and a control signal wiring line to control drive states of the light sources. The light source drive unit 20 discriminates the types of the connected light source modules 12 and 14 (16) on the basis of a discrimination signal received via the discrimination signal wiring line. For example, when the connected light source module is the first light source module 12 on which the blue semiconductor laser light source 22 is mounted, the light source drive unit is detected via the discrimination signal wiring line, and the power and control signal corresponding to the laser light source are supplied from the power wiring line and the control signal wiring line, respectively.

An example of a discriminating method of the connected light source module 12 or 14 (16) is a method in which the type or drive information of the light source is beforehand stored in an unshown storage memory in the light source module 12 or 14 (16), and read from the light source drive unit 20. Furthermore, as another method, there is contrived a method in which a terminal portion of the electric terminal 36 or 56 to be connected to the connection cable 34 or 54 is provided with a characteristic shape such as an uneven shape peculiar to the light source module, and the shape is detected by an unshown sensor mounted on the connection cable 34 or 54, to discriminate the type of the light source module 12 or 14 (16) on the basis of the detected shape. Furthermore, there is contrived a method or the like in which a unique electric signal pattern is output from the light source module 12 or 14 (16) through the discrimination signal wiring line, and the type of the connected light source module 12 or 14 (16) is discriminated from the electric signal pattern.

At this time, the control of the light source module 12 or 14 (16) is preferably appropriately regulated in accordance with not only the type of the light source module 12 or 14 (16) or a type of the irradiation module 18 connected to the light source module 12 or 14 (16). Thus, it is necessary to transmit, to the light source drive unit 20, information of the type of the irradiation module 18 connected to the light source module 12 or 14 (16). This information of the irradiation module 18 may be transmitted via the light source module 12 or 14 (16) and the connection cable 34 or 54, or by directly connecting the light source drive unit 20 to the connection unit (described later).

It is to be noted that in the present embodiment, there has been described an example where the two connection cables 34 and 54 are connected from the light source drive unit 20 toward the two light source modules, but the present invention is not limited to this example. For example, a method is also possible in which the second light source module 14 is connected to the light source drive unit 20 via the connection cable 54, to control the first light source module 12 via the connection cable 54, the second light source module 14, and the connection unit of the irradiation module 18. In this case, each of connecting portions of the first light source module 12 and the connection unit is provided with an electric connection terminal which is a control signal transmission terminal to transmit the control signal or a power supply terminal to supply the power, in addition to the first light source light entrance end (described later). At this time, this connection is preferably utilized for the discrimination signal of the type of the connected light source module.

Figure 2:
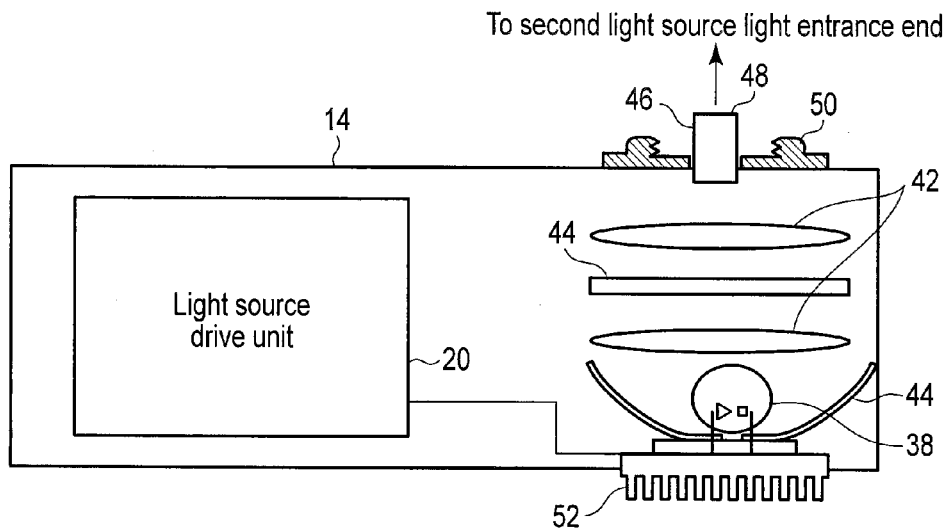
FIG. 2 is a view showing a constitution of a modification of a second light source module.

Furthermore, in the present embodiment, there has been described an example where the light source drive unit 20 is a unit separated from the light source modules 12 and 14 (16), but the present invention is not limited to this example. FIG. 2 shows a modification of the second light source module 14. In a constitution shown in FIG. 2, the light source drive unit 20 is mounted in the second light source module 14. The second light source module 14 has a large size and uses more power compared with the first light source module 12, and hence the constitution is not noticeably affected even when the light source drive unit 20 is mounted. In this case, the connection cable 34 to control the first light source module 12 is not used, but the first light source module is preferably controlled via the connection unit of the irradiation module 18.

It is to be noted that the light source drive unit 20 can also be mounted on the first light source module 12. In this case, a difference between a size of the first light source module 12+the light source drive unit 20 and a size of the second light source module 14 is small, and hence there is a merit that management of storing or the like is easily executed, or the like.

Next, the irradiation module 18 will be described.

The irradiation module 18 according to the present first embodiment includes a connection unit 62 and a light guide unit 64. On the light guide unit 64, two types of light guide members; a first light guide member 66 and a second light guide member 68 are mounted. The light source light emitted from the light source modules 12 and 14 (16) to enter after-mentioned light source light entrance ends of the connection unit 62 is guided through the light guide members 66 and 68 to light emitting ends of these light guide members, and is converted into the illuminating light by an after-mentioned optical conversion units, or is directly applied toward an illumination object. In the present embodiment, an example of the light guide unit 64 having two types of light guide members; a first light guide member 66 and a second light guide member 68, is described. The light emitting ends of the first and second light guide members 66 and 68 are connected to first and second optical conversion units 70 and 72, respectively, and here the light source light is converted into the illuminating light to be applied onto the illumination object.

Here, elements of the irradiation module 18 of the present embodiment are described.

First, the connection unit 62 is described.

The connection unit 62 is optically and mechanically connected to the light source module 12, 14 or 16, and has a connecting function of transmitting, to the light guide unit 64, the light source light emitted from the light source module 12, 14 or 16. In the present embodiment, the connection unit 62 is a substantially rectangular parallelepiped body, and on two different flat surfaces thereof, two light source light entrance ends of a first light source light entrance end 74 and a second light source light entrance end 76 are mounted.

The two light source light entrance ends 74 and 76 disposed in the connection unit 62 are the light source light entrance ends of the first and second light guide members 66 and 68, and have a common function of allowing entrance of the light source light emitted from the light source. On the other hand, the two light source light entrance ends 74 and 76 differ, as follows. That is, a first fixing portion B 78 disposed in the vicinity of the first light source light entrance end 74 can mechanically be connected to the first fixing portion A 30 disposed in the first light source module 12, but cannot mechanically be connected to a second fixing portion A 50 disposed in the second light source module 14. Furthermore, a second fixing portion B 80 disposed in the vicinity of the second light source light entrance end 76 can mechanically be connected to the second fixing portion A 50 disposed in the second light source module 14, but cannot mechanically be connected to the first fixing portion A 30 disposed in the first light source module 12.

Figure 3:
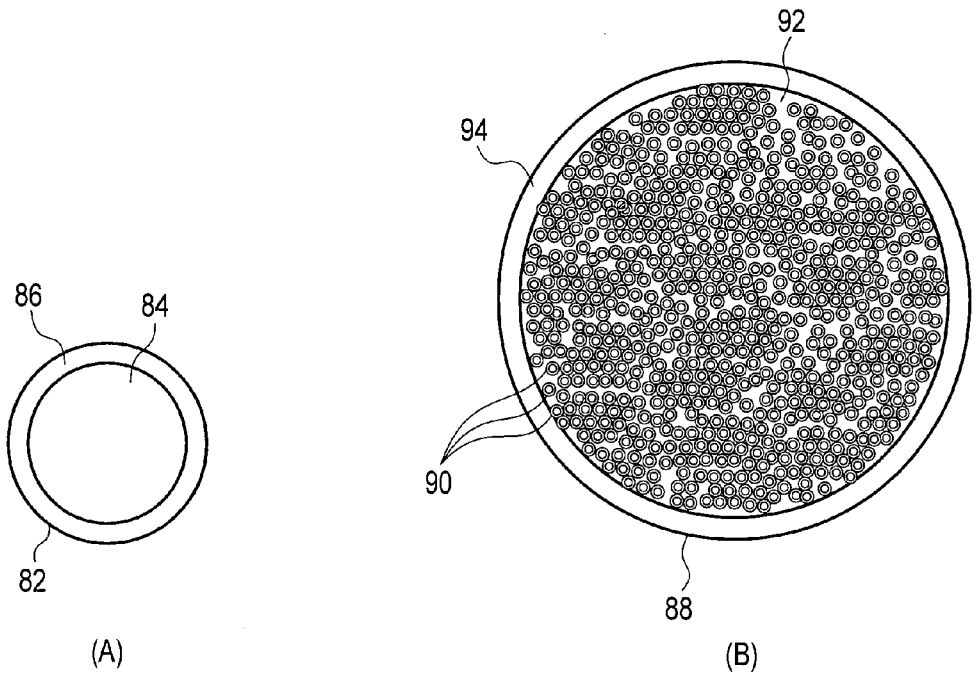
FIG. 3(A) is a view showing a cross section of a single optical fiber as a first light guide member.
FIG. 3(B) is a view showing a cross section of a light guide as a second light guide member.

In the present embodiment, the first light source light entrance end 74 is the light source light entrance end which allows the entrance of the blue laser light as the first light source light emitted from the first light source module 12 on which the blue semiconductor laser light source 22 as the first light source is mounted. Therefore, the first light source light entrance end 74 is an end portion of the single optical fiber suitable for guiding the laser light, and is held by a ferrule. As shown in FIG. 3(A), a single optical fiber 82 is one optical fiber constituted by covering a core 84 of a high refractive index with a clad 86 of a lower refractive index. To guide the laser light, an optical fiber having a core diameter of several μm to about 200 μm is suitable. For an illumination use application, a multimode optical fiber is suitable. It is to be noted that an effective entrance region of the single optical fiber 82 is a region of the core 84 as shown in FIG. 3(A).

The first light source light entrance end 74 is mechanically held by the connection mechanism to face the laser light guiding optical fiber 26 of the first light source module 12 so that central axes substantially match each other. The single optical fiber 82 passes through the connection unit 62, and extends to the light guide unit 64. That is, the single optical fiber 82 which is the first light guide member 66 substantially linearly extends in the connection unit 62 from the first light source light entrance end 74 to the vicinity of a tip portion of the light guide unit 64.

On the other hand, the second light source light entrance end 76 is connected to the second light source module 14 which is a lamp light source or the third light source module 16 which is an LED light source.

The second light source light entrance end 76 needs to efficiently receive second or third light source light from a light source such as the Xe lamp 38 or the LEDs 58 whose emission region is large as compared with the blue semiconductor laser light source 22, and hence the end is an end portion of a light guide having a large entrance region as compared with the first light source light entrance end 74. Here, as shown in FIG. 3(B), a light guide 88 is constituted of a bundle fiber, and the effective entrance region of the bundle fiber is a region 92 where bundled bare optical fibers 90 are disposed. Usually, the bundle fiber is constituted so that a periphery of the bundled bare optical fibers 90 is held in a substantially round shape by a case 94 of a metal or the like. At this time, a diameter of the effective entrance region of the bundle fiber is a bundle fiber diameter along which the bundled bare optical fibers 90 held in the substantially round shape are disposed. To guide the second or third light source light from the Xe lamp 38 or the LEDs 58, the diameter of the effective entrance region is preferably several hundred μm or more. Furthermore, when the diameter is excessively large, a diameter of the light guide unit 64 becomes large, which causes a problem sometimes, depending on the use application. Therefore, when the diameter is about 3 mm or less, also in the case of illumination of the inside of a fine hole or the like, insertion properties of the light guide unit 64 into the hole are high, which reduces concerns over a limited application range.

Furthermore, to simultaneously enable the connection of both of the first light source module 12 and the second light source module 14 to the connection unit 62, in the irradiation module 18 according to the present embodiment, the first and second light source light entrance ends 74 and 76 are disposed on two mutually perpendicular surfaces of the connection unit 62 having a substantially rectangular parallelepiped shape. In the light guide unit 64, the first light guide member 66 and the second light guide member 68 are disposed in parallel, and hence in the connection unit 62, it is necessary to bend at least one optical path. In the present embodiment, the bendable bundle fiber is used in the second light guide member 68, and hence the bundle fiber is bent and mounted as shown in FIG. 1.

Next, the light guide unit 64 will be described.

In the light guide unit 64, the light source light emitted from the light source is guided to an illuminating light emitting end. To enable the emission of the illuminating light at a desirable position or in a desirable direction, the single optical fiber 82 and the light guide 88, which are freely curvable, are selected as the light guide members 66 and 68 in the present embodiment.

On the light guide unit 64, two light guide members; the first light guide member 66 and the second light guide member 68, are mounted in parallel, and the light guide members are covered with a light guide unit cover 96. One end of the light guide unit 64 is connected to the connection unit 62. In the light guide members mounted on the light guide unit 64, the single optical fiber 82 which is the first light guide member 66 passes through the connection unit 62 from the first light source light entrance end 74, to extend to the first optical conversion unit 70 mounted in the light guide unit 64. Furthermore, the light guide 88 which is the second light guide member 68 passes through the connection unit 62 from the second light source light entrance end 76, to extend to the second optical conversion unit 72 mounted in the light guide unit 64.

As described above, the light guide 88 which is the second light guide member 68 guides the second or third light source light from the Xe lamp 38 or the LEDs 58 having a large emission region as compared with the blue semiconductor laser light source 22, and hence the bundle fiber whose effective entrance region is large is used. The bundle fiber is constituted by bundling the several hundred to several thousand bare optical fibers 90. The bundle fiber passes through the connection unit 62 to extend to the second light source light entrance end 76. That is, the bundle fiber is bent and disposed in the connection unit 62 as shown in FIG. 1.

It is to be noted that optical specifications of the first and second light guide members 66 and 68 are preferably set so that the optical specifications correspond to optical characteristics of the light source light to be guided. In the present embodiment, the first light guide member 66 has a purpose of guiding the blue laser light as the first light source light. An emission point of the laser light is small, and hence the laser light can easily be made to enter a small entrance region by a lens or the like. Therefore, of the optical specifications required of the first light guide member 66, a light transmittancy in a wavelength range of 370 nm to 500 nm, which is a wavelength range of a blue region, is preferably high. Furthermore, a numerical aperture NA does not have to be so large. For example, as the first light guide member 66, it is possible to use a usual laser light guiding single optical fiber having an NA of about 0.2 to 0.4.

On the other hand, it is presumed that the second light guide member 68 guides the second or third light source light in which an emission point is large, a radiation angle is also large and further, a wavelength range is large as in the light from the Xe lamp 38 or the LEDs 58. Therefore, of the optical specifications required of the second light guide member 68, the numerical aperture NA is preferably large to cope with the large radiation angle. Therefore, as the second light guide member 68, the bare optical fibers 90 having a numerical aperture NA larger than that of the first light guide member 66 are preferably used. Furthermore, the light guide member guides light of a large wavelength range, and hence the member is preferably comparatively flat for light from visible light to light of a near-infrared region, but there is less necessity for an especially high transmittance for light of a blue region, where visibility is comparatively low.

In summary of the above description, the optical specifications required of the first light guide member 66 and the second light guide member 68 are compared as follows.

(1) The effective entrance region of the second light guide member 68 is preferably larger than that of the first light guide member 66.

(2) The numerical aperture NA of the second light guide member 68 is preferably larger than that of the first light guide member 66.

(3) The light transmittancy of the first light guide member 66 is preferably higher than that of the second light guide member 68 in the blue region.

It is to be noted that the light transmittancy of the above (3) is set to the transmittancy of the blue region, because the blue semiconductor laser light source 22 is used in the present embodiment. When a light source of a region other than the blue region is used, the transmittancy of a peak wavelength of the light source is preferably high. Therefore, the above (3) is as follows.

(3') The light transmittancy of the first light guide member 66 is preferably higher than that of the second light guide member 68 at a wavelength 2 which is the peak wavelength of the light source light to be guided by the first light guide member 66.

It is to be noted that in the present embodiment, there has been described the example where as the first light guide member 66 combined with the blue semiconductor laser light source 22 to guide the blue laser light, the single optical fiber 82 is used, and as the second light guide member 68 combined with a light source such as the Xe lamp 38 or the LEDs 58 to guide the lamp light or the LED light, the light guide 88 which is the bundle fiber obtained by bundling the bare optical fibers 90 is used, but the present invention is not limited to this example. For example, on the substrate or a film, an optical waveguide path obtained by patterning or laminating members having different refractive indexes can be used. In the optical waveguide path, light guide paths can be separated or combined, or various complicated optical paths can be patterned. At this time, the effective entrance region is a light guide region which is a region where the refractive index is high at an entrance end surface. In the case of the light guide path which is not round, the optical specifications can be investigated by using an area of the light guide path in place of a diameter thereof.

Furthermore, as another example of the light guide path, a single optical fiber having a core diameter of several hundred microns or more can be used in place of the bundle fiber. When the effective entrance region is the same, the light from the Xe lamp 38 or the LEDs 58 whose emission region is large can more efficiently be guided by using the single optical fiber having a large diameter compared with the bundle fiber. However, the single optical fiber having a large core diameter is not easily bent, and hence the fiber is not suitable when flexibility is required of the light guide unit 64.

The light guide members of various optical specifications can be used in accordance with a size of the emission region of the light source or a use purpose of the light source device without departing from the gist of the present invention.

Next, the optical conversion units 70 and 72 will be described.

The optical conversion unit 70 or 72 has a function of converting the light source light emitted from the light source into desirable illuminating light. For example, the light emitting member has a function of controlling a luminous intensity distribution of the light source light emitted from the light guide member 66 or 68, or controlling a wavelength, a spectrum shape or an intensity of light.

The optical conversion unit 70 or 72 is disposed on an illuminating light emitting end side of the light guide unit 64.

In the present embodiment, as the first optical conversion unit 70, there is mounted a spectrum conversion member which absorbs a part of the blue laser light emitted from the blue semiconductor laser light source 22 as the first light source to emit converted yellow fluorescence, and scatters and emits the remaining blue laser light. As this spectrum conversion member, for example, a wavelength conversion member can be used in which a fluorescent powder of YAG:Ce or the like is dispersed in a resin or glass. The wavelength conversion member can convert the peak wavelength, spectrum shape, and luminous intensity distribution which are optical properties of the blue laser light.

The first optical conversion unit 70 is optically connected to the first light guide member 66, and allows entry of the blue laser light which is the first light source light guided by the first light guide member 66. Furthermore, the first optical conversion unit 70 is not optically connected to the second light guide member 68, and does not allow entry of the lamp light or the LED light which is the second or third light source light guided by the second light guide member 68.

Furthermore, as the second optical conversion unit 72, there is mounted a radiation angle conversion member, which is a type of luminous intensity distribution conversion member, to enlarge an emission angle of the second light source light from the Xe lamp 38 as the second light source. In the radiation angle conversion member, for example, there is used one concave lens, or a lens group which converts a radiation angle into a desirable radiation angle by a combination of lenses. By the radiation angle conversion member, the peak wavelength or the spectrum shape of the lamp light from the Xe lamp 38 hardly changes, and the only radiation angle can be converted.

The second optical conversion unit 72 is optically connected to the second light guide member 68, and allows the entrance of the lamp light or the LED light which is the second or third light source light guided by the second light guide member 68. Furthermore, the second optical conversion unit 72 is not optically connected to the first light guide member 66, and does not allow entry of the blue laser light which is the first light source light guided by the first light guide member 66. That is, the lamp light which is the second light source light emitted from the Xe lamp 38 includes a blue component which can be absorbed by the spectrum conversion member mounted on the first optical conversion unit 70 and converted into yellow fluorescence. Therefore, when the second light guide member 68 is optically connected to the first optical conversion unit 70, the illuminating light including the yellow fluorescence is applied even in a case where only the second light source light from the Xe lamp 38 is to be applied. To avoid this problem, the first optical conversion unit 70 is constituted to be optically separate from the second light guide member 68.

It is to be noted that in the present embodiment, there has been described an example of the light guide unit 64 on which the above-mentioned spectrum conversion member and the above-mentioned luminous intensity distribution conversion member are mounted as the optical conversion units 70 and 72, but the present invention is not limited to this example. For example, such various optical members as described in the following can be used as the optical conversion units 70 and 72. Furthermore, these members can be combined and used.

(1) As the luminous intensity distribution conversion member, it is possible to use a radiation angle conversion member such as a convex lens or a combination of the convex lens and a concave lens, in addition to the concave lens, which converts the radiation angle, or a luminous intensity distribution conversion member such as a hologram lens or a diffraction lattice which changes the radiation angle or converts a direction of the light to be radiated, i.e., an orientation.

(2) As the luminous intensity distribution conversion member, it is possible to use a member in which particles of alumina or the like having a high refractive index and a high reflectance are dispersed in a resin or glass, a member in which transparent members having different refractive indexes are mixed, a scattering plate such as ground glass, a diffusion plate in which micro uneven portions are disposed in the surface, or the like.

(3) As the spectrum conversion member, in addition to a fluorescent body, it is possible to use an optical semiconductor, a member which generates secondary higher harmonic waves (SHG), an electroluminescence material, or the like.

(4) As an optical transmission modulation member which transmits a part of the light source light and blocks a part thereof, it is possible to use various optical filters, or a member such as a dyestuff or an optical resonator (etalon) having wavelength selecting properties.

(5) As the optical transmission modulation member which transmits a part of the light source light and blocks a part thereof, it is possible to use an optical switch, or a member such as an electrochromic member or a liquid crystal device having space selecting properties.

For example, (2) is suitable for safety of the laser light source or removal of speckles. Furthermore, when the radiation angle of the lamp light or the LED light is regulated, (1) or (2) can be used.

Next, there will be described an operation of the light source system 10 including the irradiation module 18 according to the present embodiment.

First, there is described the operation when the first light source module 12 is combined with the irradiation module 18 according to the present embodiment.

The first light source module 12 is connected to the irradiation module 18 to constitute the light source device. The blue semiconductor laser light source 22, which is the first light source mounted on the first light source module 12, emits the blue laser light as the first light source light in response to the control signal from the light source drive unit 20 connected to the first light source module 12. The blue laser light as the first light source light emitted from this blue semiconductor laser light source 22 is applied onto the spectrum conversion member mounted on the first optical conversion unit 70 via the laser light guiding fiber 26, the first light source light emitting end 28, the first light source light entrance end 74, and the first light guide member 66. The spectrum conversion member absorbs a part of the blue laser light to convert the wavelength into that of the yellow fluorescence, and diffuses and emits the remaining part to the outside. A light intensity ratio between the blue laser light and the yellow fluorescence to be emitted to the outside is set so that the mixed light becomes the white light, by regulating a thickness, concentration, shape or the like of the fluorescent body in the spectrum conversion member. In the blue semiconductor laser light source 22, as compared with the Xe lamp 38, the LEDs 58 or the like, extraordinary miniaturization and power saving are possible, and hence the light source device achieved by this combination is a small and highly efficient light source device. Therefore, the light source device is very effective for a use application in which the device is to be miniaturized or a use application in which battery drive or the like is required.

Next, there will be described an operation of a light source device in which the second light source module 14 is combined with the irradiation module 18 according to the present embodiment.

The second light source module 14 is connected to the irradiation module 18 to constitute the light source device. The Xe lamp 38 which is the second light source mounted on the second light source module 14 emits the lamp light as the second light source light in response to the control signal from the light source drive unit 20 connected to the second light source module 14. The lamp light which is the second light source light emitted from this Xe lamp 38 is applied onto the radiation angle control member mounted on the second optical conversion unit 72 via the light guide rod 46, a second light source light emitting end 48, the second light source light entrance end 76, and the second light guide member 68. The concave lens which is the radiation angle control member spreads the lamp light at a desirable spread angle to emit the light toward an unshown illumination object.

The lamp light which is the second light source light from the Xe lamp 38 is white light having a spectrum comparatively close to sunlight, and is therefore effective when observation using the light close to sunlight is required.

Next, there will be described an operation of a light source device in which the third light source module 16 is combined with the irradiation module 18 according to the present embodiment.

The third light source module 16 is connected to the irradiation module 18 to constitute the light source device.

The LEDs 58 which constitute the third light source mounted on the third light source module 16 emit the LED light as the third light source light in response to the control signal output from the light source drive unit 20 connected to the third light source module 16. The subsequent operation is similar to the operation in the case where the second light source module 14 is connected.

In the LEDs 58 which constitute the third light source, light of various emission colors can be utilized. Furthermore, when the multiplexing optical system 60 is used as in the present embodiment, it is possible to emit the mixed light of various colors required for the illumination. Furthermore, as compared with the second light source which is the Xe lamp 38, a small power-saving light source can be realized.

As described above, in the present first embodiment, the irradiation module 18 on which the light guide members 66 and 68 are mounted is appropriately combined with the light source module 12, 14, or 16, so that various illuminating light for purposes can be emitted from the one irradiation module 18.

That is, when efficient bright white light is required, the light can be realized by combining the first light source module 12 with the irradiation module 18. Furthermore, when the light having the spectrum close to sunlight is required, the second light source module 14 may be used.

At this time, the common light guide member (the second light guide member 68) is usable for light sources such as the LEDs 58 and the Xe lamp 38 which emit the light of similar characteristics, which obviates the need to increase the number of the light guide members. The LEDs 58 and the Xe lamp 38 are common in that the emission regions are comparatively large, the optical characteristics are close, and hence the bundle fiber having the optical specifications corresponding to optical characteristics of the light sources is suitable as the light guide member. Furthermore, the light sources are also common in that the second or third light source light emitted from the second light source light emitting end 48 of the light source module 14 or 16 is applied onto the illumination object without converting the spectrum or the peak wavelength of the light, and the second optical conversion unit 72 can be used also in common as an optical conversion member.

On the other hand, in a combination of the semiconductor laser light source and the spectrum conversion member of the first optical conversion unit 70, a behavior of the first optical conversion unit 70 varies in accordance with the wavelength of the semiconductor laser light source. For example, in the spectrum conversion member in which there is used the YAG;Ce fluorescent body illustrated in the present embodiment, the blue laser light is absorbed to convert the wavelength into that of the yellow fluorescence, but blue purple laser light or laser light of a wavelength longer than that of green is not absorbed, and hence the wavelength is not converted. However, this spectrum conversion member functions as a diffusion unit which diffuses the laser light irrespective of the wavelength of the entering laser light. As a result, when the blue laser light enters the first optical conversion unit 70, the white illuminating light is emitted from the unit by the above-mentioned operation, but when the blue purple laser light or the laser light of a wavelength longer than that of green enters the unit, the unit functions as the luminous intensity distribution conversion member which diffuses the laser light. In this way, when the light guide path of the single optical fiber is used, the illuminating light can be emitted by appropriately combining the wavelength of the laser light with the optical conversion unit.

Second Embodiment

Figure 4:
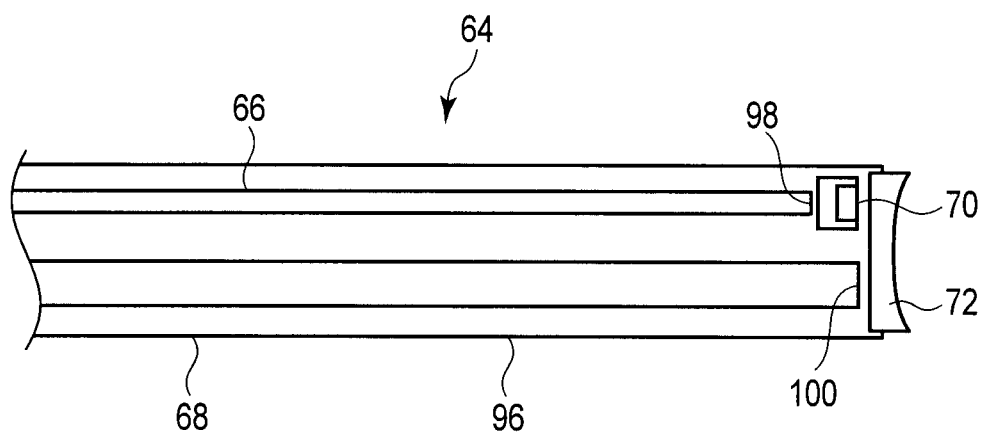
FIG. 4 is a view showing a constitution of an irradiation module having light guide members according to a second embodiment of the present invention.

Next, an irradiation module 18 according to a second embodiment of the present invention will be described with reference to FIG. 4.

The irradiation module 18 according to the present embodiment is different from the first embodiment in a constitution of a light guide unit 64, and similar to the first embodiment in other respects. Therefore, description of the parts similar to those of the above first embodiment is omitted, and only different parts will be described.

The present embodiment is different from the first embodiment in that a second optical conversion unit 72 mounted on the light guide unit 64 of the irradiation module 18 is optically connected to both of a first light guide member 66 and a second light guide member 68.

That is, blue laser light which is first light source light guided by the first light guide member 66 and emitted from a first light emitting end 98 as the light emitting end of the first light guide member 66 enters a first optical conversion unit 70, and here the light is converted into white light and emitted similarly to the first embodiment. The white light emitted from the first optical conversion unit 70 then enters the second optical conversion unit 72 where a luminous intensity distribution of the light is converted, and the light is applied as illuminating light onto an illumination object. It is to be noted that lamp light which is second light source light guided by the second light guide member 68 and emitted from a second light emitting end 100 as the light emitting end of the second light guide member 68 enters into the second optical conversion unit 72, whereby a luminous intensity distribution of the light is converted, and the light is emitted to the illumination object. This constitution is similar to the first embodiment.

A basic operation of a light source system 10 including the irradiation module 18 according to the present second embodiment of the above-mentioned constitution is similar to that of the above first embodiment.

As described above, according to the irradiation module 18 of the present second embodiment, the light emitted from the first optical conversion unit 70 and the lamp light as the second light source light emitted from the second light emitting end 100 of the second light guide member 68 are optically converted by the common optical conversion unit (the second optical conversion unit 72), and hence properties of the two illuminating light, for example, the luminous intensity distributions can be set to the same characteristics. Furthermore, the first optical conversion unit 70 does not need to have a function of regulating the luminous intensity distribution, and hence this unit is easily miniaturized. Furthermore, the second light guide member 68 is a bundle fiber an entrance region of which is constituted to be large to cope with a light source such as a lamp with a large emission region. On the other hand, the first light guide member 66 is a single optical fiber with a small entrance region to cope with a light source such as a laser with a small emission region. Therefore, thicknesses of the two light guide members 66 and 68 are noticeably different. According to the constitution of the present embodiment, the first light guide member 66 is easily disposed close to the second light guide member 68, and hence a diameter of the irradiation module 18 can easily be made to be small.

It is to be noted that there has been described the example where the spectrum conversion member and the luminous intensity distribution conversion member are used as the first optical conversion unit 70 and the second optical conversion unit 72 described in the present embodiment, respectively, but the present invention is not limited to this example. It is possible to use one of various optical conversion elements described in the above first embodiment alone, or an appropriate combination of the elements.

The present invention has been described above on the basis of the embodiments, but the present invention is not limited to the above-mentioned embodiments, and needless to say, various modifications or applications are possible within the gist of the present invention.

For example, in the above embodiments, there has been described the example where the first light guide member 66 guides the blue semiconductor laser light from the blue semiconductor laser light source 22 to the spectrum conversion member having YAG:Ce and mounted on the first optical conversion unit 70, and here the light is converted into white light, but the present invention is not limited to this example. In place of such a spectrum conversion member, for example, it is possible to combine one conventional fluorescent body or fluorescent bodies which receive the blue purple semiconductor laser light to convert the light into white light. In consequence, it is possible to realize white light of a broader spectrum. Furthermore, illuminating light of various colors can be realized by combining the fluorescent body which converts the spectrum into not only white color but also a desirable color. It is to be noted that in these constitutions, if necessary, it can suitably be selected whether or not to emit the diffusing light of the laser light to the outside.

Furthermore, in the above embodiments, there has been described the example where the semiconductor laser light source is used as the first light source to be combined with the single optical fiber 82 which is the first light guide member 66, but the present invention is not limited to this example. Any one of light sources such as a super luminescent diode (SLD) and various laser light sources can be used, as long as the light source is easily optically combined with the light guide member in which the emission region is small and the effective entrance region is small. Furthermore, there has been described the example where the Xe lamp 38 and the LEDs 58 are used as the light sources to be combined with the light guide 88 which is the second light guide member 68, but the present invention is not limited to this example. Any one of light sources such as a fluorescent tube and an EL light emitting material can be used, as long as the light source has a comparatively large emission region.

Furthermore, the light source is not limited to the blue semiconductor laser light source 22, and it is possible to use various laser light sources such as a semiconductor laser of another color, a solid laser, and a gas laser. At this time, when the laser light is to be emitted in its color as it is, the light source can be combined and used with a luminous intensity distribution conversion unit such as a diffusion plate.

Furthermore, it is also possible to use a white laser, a super continuum light source or the like.

Also as to the lamp, the example where the Xe lamp 38 is used has only been described, but the present invention is not limited to this example. It is possible to use various lamps, for example, an electric discharge type lamp other than the Xe lamp, and a filament type lamp such as a halogen lamp.

Furthermore, in the above-mentioned embodiments, each of the light source modules 12, 14, and 16 to be connected to the irradiation module 18 has one light source, but the present invention is not limited to this example. For example, it is possible to realize a light source module having both a semiconductor laser and a lamp. At this time, in the connection of the light source module to the irradiation module 18, one mechanical connecting portion may be provided with two light source light entrance ends, or the ends may be disposed separately from each other.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An irradiation module mechanically detachably attached to a plurality of light source modules, the plurality of light source modules comprising a first light source module and a second light source module, the irradiation module comprising:
   a first light source light entrance end which allows entry of the first light source light emitted from the first light source module;
   a first optical fiber to guide the first light source light which has entered the first light source light entrance end;
   a second light source light entrance end which allows entry of the second light source light that is emitted from the second light source module having light source characteristics different from that of the first light source module and has optical characteristics different from that of the first light source light;
   a second optical fiber to guide the second light source light which has entered the second light source light entrance end;
   a first connector; and
   a second connector, that are configured to mechanically connect and selectively connect the first light source module and the second light source module to the irradiation module, and wherein the first connector is configured to engage with a first light source connector of the first light source module and the second connector is configured to engage with a second light source connector of the second light source module,
   wherein the first optical fiber and the second optical fiber have optical specifications in which the optical characteristics are different from each other corresponding to optical characteristics of the light source light to be guided, and
   each of the first light source module and the second light source module are selectively and detachably connectable to the irradiation module, wherein the first and second connectors are on a proximal side of the first and second optical fibers inside the irradiation module.

2. The irradiation module according to claim 1, wherein the first optical fiber and the second optical fiber are disposed in parallel in a vicinity of a light emitting end of each of the optical fibers,
   the irradiation module further comprising:
   a first optical converter which is optically connected to the light emitting end of the first optical fiber and optically separate from the second optical fiber, and converts at least one of a peak wavelength, a spectrum shape, a luminous intensity distribution, and an intensity of light in the optical characteristics of the first light source light emitted from the light emitting end of the first optical fiber, to emit thus converted light as first converted light.

3. The irradiation module according to claim 2, further comprising:

a second optical converter which is optically connected to the light emitting end of the second optical fiber, and converts at least one of a peak wavelength, a spectrum shape, a luminous intensity distribution, and an intensity of light in the optical characteristics of the second light source light emitted from the light emitting end of the second optical fiber, to emit thus converted light as second converted light.

4. The irradiation module according to claim 3, wherein the second optical converter is optically separate from the light emitting end of the first optical fiber.

5. The irradiation module according to claim 4, wherein the second optical converter is one lens or plural lenses, or a diffusion plate which regulates entered light into a desirable luminous intensity distribution.

6. The irradiation module according to claim 3, wherein the first optical converter is a wavelength converter having a function of converting all of the peak wavelength, the spectrum shape, and the luminous intensity distribution in the optical characteristics of the first light source light emitted from the light emitting end of the first optical fiber.

7. The irradiation module according to claim 6, wherein the first optical converter and the second optical converter have different light conversion characteristics corresponding to optical characteristics of the first light source light and optical characteristics of the second light source light, respectively.

8. The irradiation module according to claim 3, wherein the second optical converter is further optically connected to the light emitting end of the first optical fiber, receives both of the first converted light emitted from the light emitting end of the first optical fiber and the second optical fiber light emitted from the light emitting end of the second optical fiber, and converts each of the light to emit the converted light.

9. The irradiation module according to claim 3, wherein the first optical converter is a luminous intensity distribution converter having a function of converting the luminous intensity distribution without converting the peak wavelength and the spectrum shape in the optical characteristics of the first light source light emitted from the light emitting end of the first optical fiber.

10. The irradiation module according to claim 1, wherein the optical specifications of the first optical fiber and the second optical fiber include a dependence of a light transmittance on a wavelength, and
the light transmittance at a wavelength $\lambda$ which is the peak wavelength of the first light source light to be guided by the first optical fiber is higher than that at the wavelength $\lambda$ of the second optical fiber.

11. The irradiation module according to claim 10, wherein the first light source emits blue region light having a wavelength of 370 nm to 500 nm,
the irradiation module further comprising:
a first wavelength converter which is optically connected to the first optical fiber on side of the emitting end of the first optical fiber, and absorbs the blue region light to emit white light.

12. The irradiation module according to claim 11, wherein the second light source is the white light source.

13. The irradiation module according to claim 12, wherein the blue light source is a semiconductor laser light source, and the second light source is an LED light source or a lamp light source.

14. The irradiation module according to claim 1, wherein the optical specifications of the first and second optical fibers include a light source light entrance region, and an effective light source light entrance region of the second optical fiber is larger than an effective light source light entrance region of the first optical fiber.

15. The irradiation module according to claim 14, wherein the first optical fiber is a single optical fiber comprising one optical fiber,
the second optical fiber is a fiber constituted by bundling bare optical fibers, and
a core diameter of the single optical fiber which is the first optical fiber is smaller than a diameter of the bundle fiber constituted by bundling the bare optical fibers of the optical fiber which is the second optical fiber.

16. The irradiation module according to claim 15, wherein the first light source light to be guided by the first optical fiber is light from a semiconductor laser light source or a super luminescent light source.

17. The irradiation module according to claim 15, wherein the second light source light to be guided by the second optical fiber is light from an LED light source or a lamp light source.

18. The irradiation module according to claim 14, wherein each of the first optical fiber and the second optical fiber is a single optical fiber, and
a core diameter of the single optical fiber which is the first optical fiber is smaller than a core diameter of the single optical fiber which is the second optical fiber.

19. The irradiation module according to claim 18, wherein the first light source is a semiconductor laser light source or a super luminescent light source.

20. The irradiation module according to claim 18, wherein the second light source light is an LED light source or a lamp light source.

21. The irradiation module according to claim 14, wherein a numerical aperture of the first optical fiber is smaller than that of the second optical fiber.

22. The irradiation module according to claim 21, wherein the first light source is a semiconductor laser light source or a super luminescent light source.

23. The irradiation module according to claim 21, wherein the second light source is an LED light source or a lamp light source.

24. The irradiation module according to claim 1, wherein the first and second connectors are on an outer periphery of a connection unit and a portion of the first and second optical fibers is inside the connection unit.

25. The irradiation module according to claim 24, wherein the first and second connectors are on two different surfaces of the connection unit.

26. The irradiation module according to claim 24, wherein the first optical fiber and the second optical fiber are bent at different angles within the connection unit.

27. A light source system comprising:
the irradiation module according to claim 1; and
a plurality of light source modules to which the irradiation module is mechanically detachably attached, wherein the plurality of light source modules comprises a first light source module having a first light source and a second light source module having a second light source.

28. The light source system according to claim 27, wherein the first light source module is the first light source module of claim 1 and the second light source module is the second light source module of claim 1.

29. The irradiation module according to claim 1, wherein the first connector is not connectable with the second light source connector and the second connector is not connectable with the first light source connector.

30. The irradiation module according to claim 1, wherein the first connector has a first diameter, the second connector has a second diameter, and wherein the first diameter is different than the second diameter.

31. The irradiation module according to claim 1, wherein the first connector is configured to engage the first light source connector threadingly and the second connector is configured to engage the second light source connector threadingly.

32. The irradiation module according to claim 1, wherein the first connector and the first light source connector have complementary uneven shapes to selectively engage each other, and the second connector and the second light source connector have complementary uneven shapes to selectively engage each other.

33. The irradiation module according to claim 1, wherein the first light source module and the second light source module are configured to be mounted directly to the irradiation module.

* * * * *